(12) United States Patent
Fisher et al.

(10) Patent No.: US 7,913,690 B2
(45) Date of Patent: Mar. 29, 2011

(54) METHOD FOR CONTINUOUS MEASUREMENT OF FLUX OF GASES IN THE LUNGS DURING BREATHING

(76) Inventors: Joseph Fisher, Toronto (CA); David Preiss, Toronto (CA); Takafumi Azami, Toronto (CA); Alex Vesely, Toronto (CA); Eitan Prisman, Toronto (CA); Tehilla Adams, Toronto (CA)

( * ) Notice: Subject to any disclaimer, the term of this patent is extended or adjusted under 35 U.S.C. 154(b) by 1591 days.

(21) Appl. No.: 10/509,068

(22) PCT Filed: Mar. 21, 2003

(86) PCT No.: PCT/CA03/00399
§ 371 (c)(1),
(2), (4) Date: Mar. 17, 2005

(87) PCT Pub. No.: WO03/082390
PCT Pub. Date: Oct. 9, 2003

(65) Prior Publication Data
US 2005/0217671 A1    Oct. 6, 2005

(30) Foreign Application Priority Data
Mar. 28, 2002    (CA) .................................... 2379353

(51) Int. Cl.
*A61M 11/00*    (2006.01)
(52) U.S. Cl. ............................ 128/204.23; 128/204.21
(58) Field of Classification Search .................. 702/22, 702/31, 32, 19; 128/204.19, 204.21–204.29, 128/205.12
See application file for complete search history.

(56) References Cited

U.S. PATENT DOCUMENTS

| | | | |
|---|---|---|---|
| 4,401,115 A | 8/1983 | Monnier | |
| 4,883,051 A * | 11/1989 | Westenskow et al. | ... 128/204.21 |
| 5,320,093 A * | 6/1994 | Raemer | ..................... 128/203.12 |
| 5,660,171 A * | 8/1997 | Kimm et al. | ............. 128/204.23 |
| 5,806,513 A * | 9/1998 | Tham et al. | .............. 128/204.22 |
| 6,354,292 B1 | 3/2002 | Fisher | |
| 6,581,599 B1 * | 6/2003 | Stenzler | ................... 128/204.23 |
| 6,622,725 B1 | 9/2003 | Fisher et al. | |
| 2002/0020410 A1 * | 2/2002 | Rydin et al. | ............. 128/200.24 |

FOREIGN PATENT DOCUMENTS
JP    2000346214    12/2000
WO    WO 98/41266    9/1998

* cited by examiner

*Primary Examiner* — Steven O Douglas
(74) *Attorney, Agent, or Firm* — Herman & Millman

(57) ABSTRACT

A method of calculating the flux of any gas (x) in a CBC circuit for a ventilated or a spontaneous breathing subject, for example said gas(x) being; a) an anesthetic such as but limited to; i)$N_2O$; ii) sevoflurane; iii) isoflurane; iv) halothane; v) desflurame; or the like b) Oxygen; c) Carbon dioxide; or the like utilizing the following relationships; Flux of gas(x)=SGF ($F_{SX}$–$F_{EX}$) wherein SGF=Source of gas flow into the breathing circuit (CBC circuit) in liters/minute as read from the gas flow meter as set by the anesthesiologist; $F_{SX}$=Fractional concentration of gas X in the source gas (which is set by the anesthesiologist); $F_{EX}$=Fractional concentration of gas X in the end expired gas as determined by a portable gas analyzer, or the like.

24 Claims, 11 Drawing Sheets

Schematic diagram of circle anaesthetic circuit

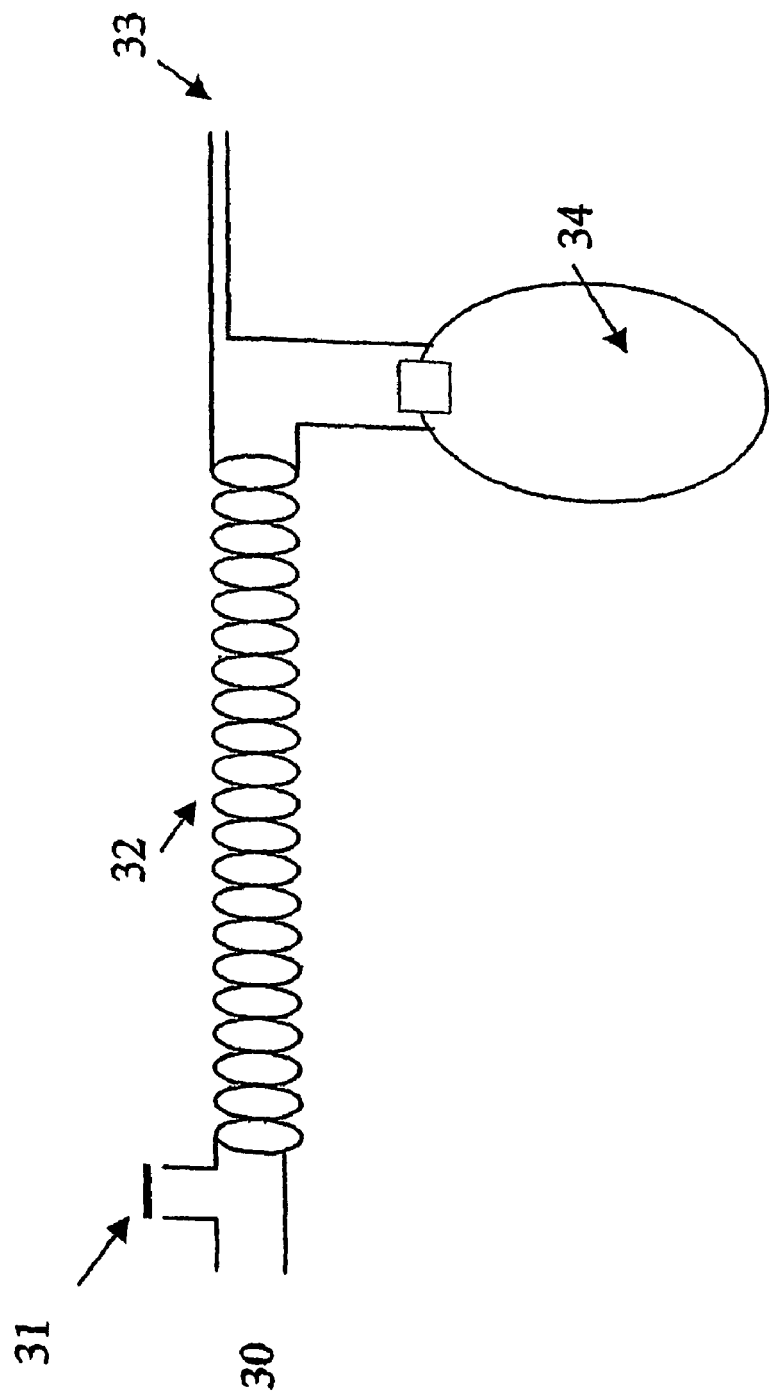
Figure 1: Schematic diagram of Magill circuit, Mapleson A configuration

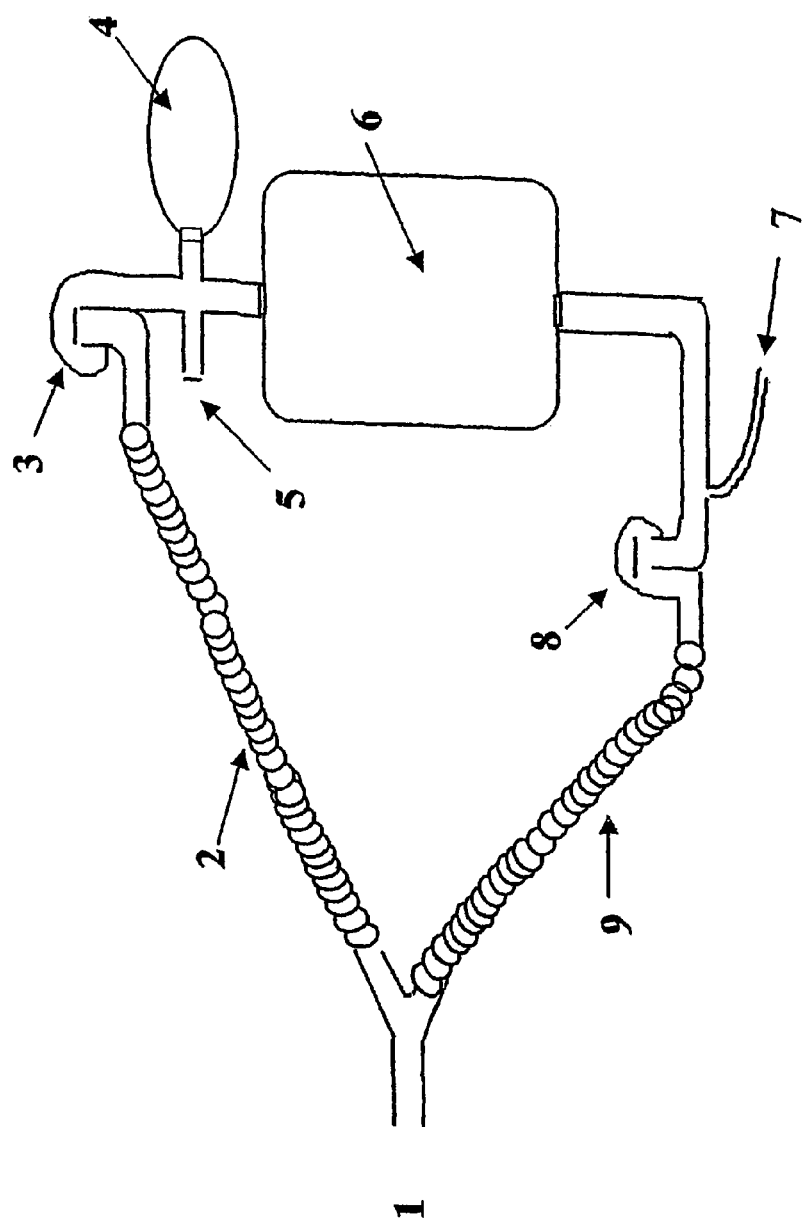
Figure 2. Schematic diagram of circle anaesthetic circuit

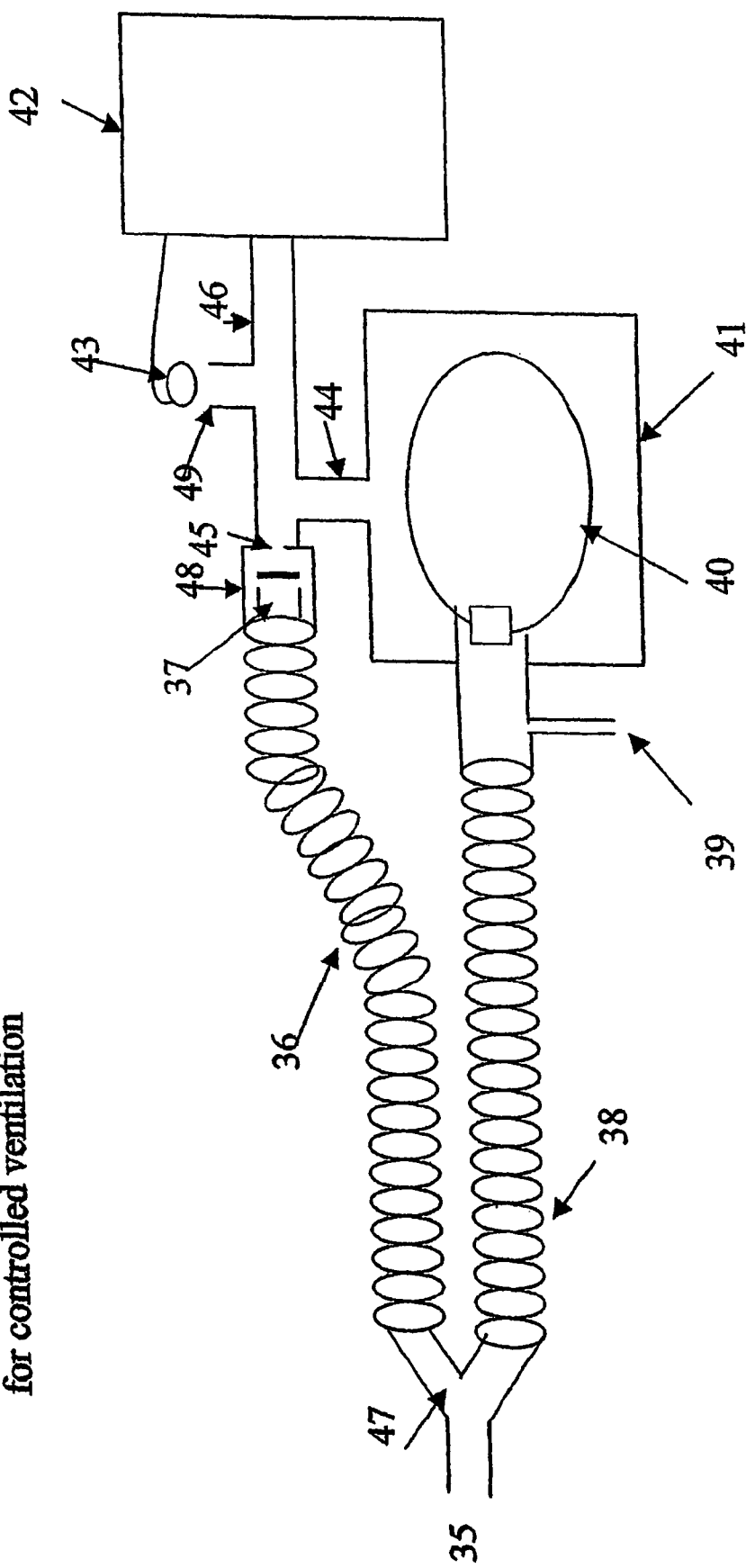
Figure 3: Schematic diagram of Magill circuit, Mapleson A configuration for controlled ventilation

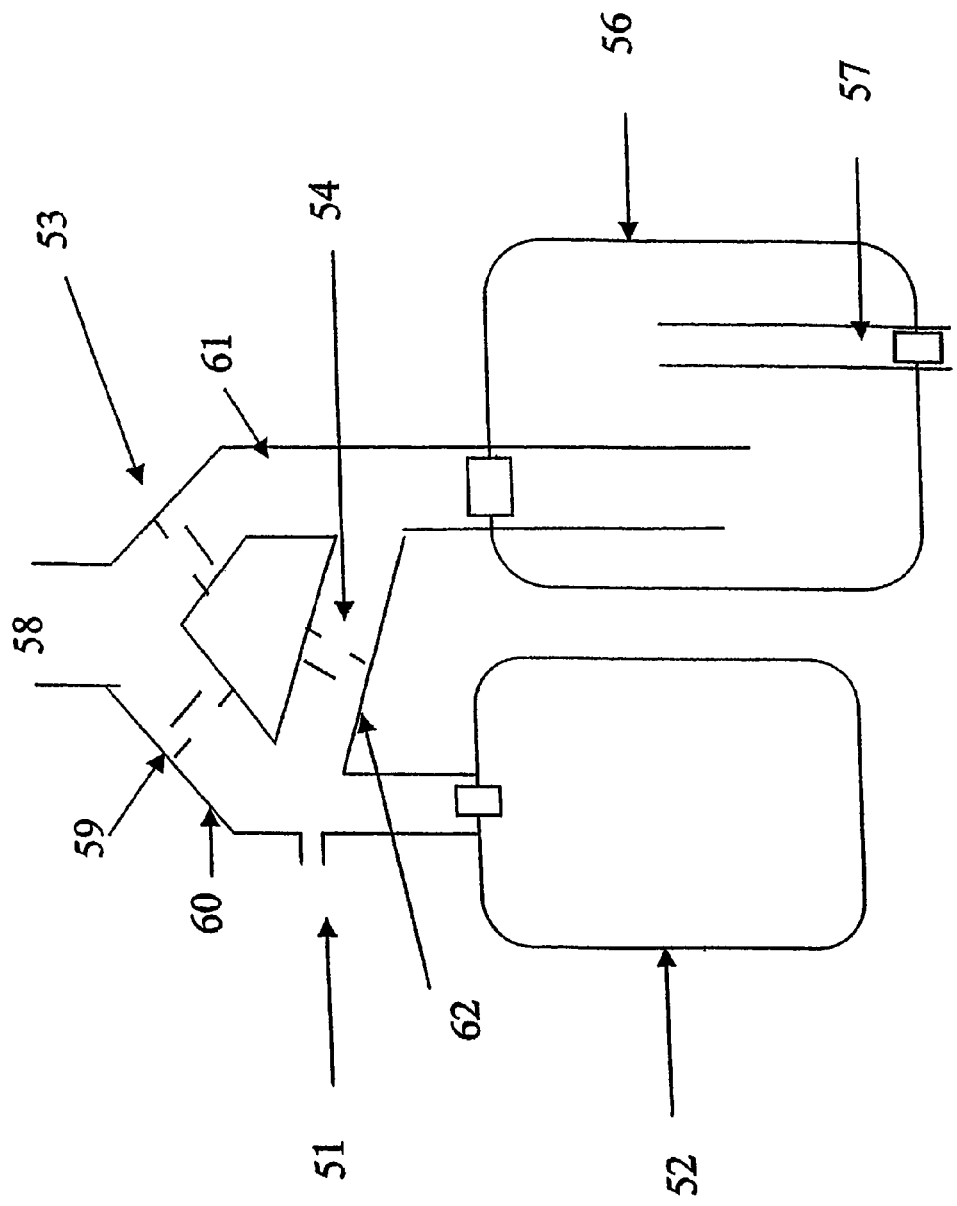
*Figure 4: Schematic diagram of rebreathing isocapnia circuit for spontaneous ventilation*

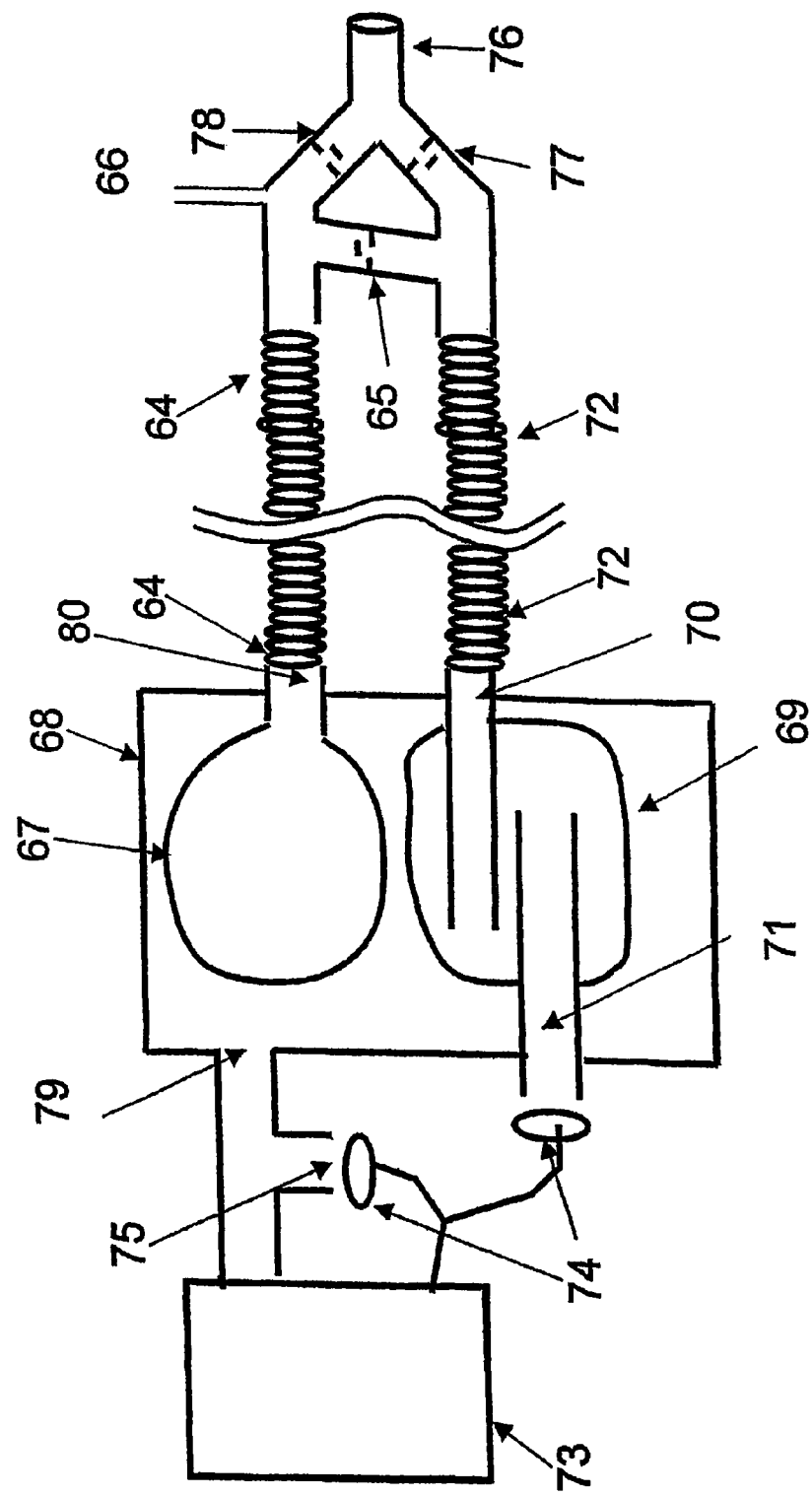
Figure 5. Schematic diagram of rebreathing isocapnia circuit for controlled ventilation

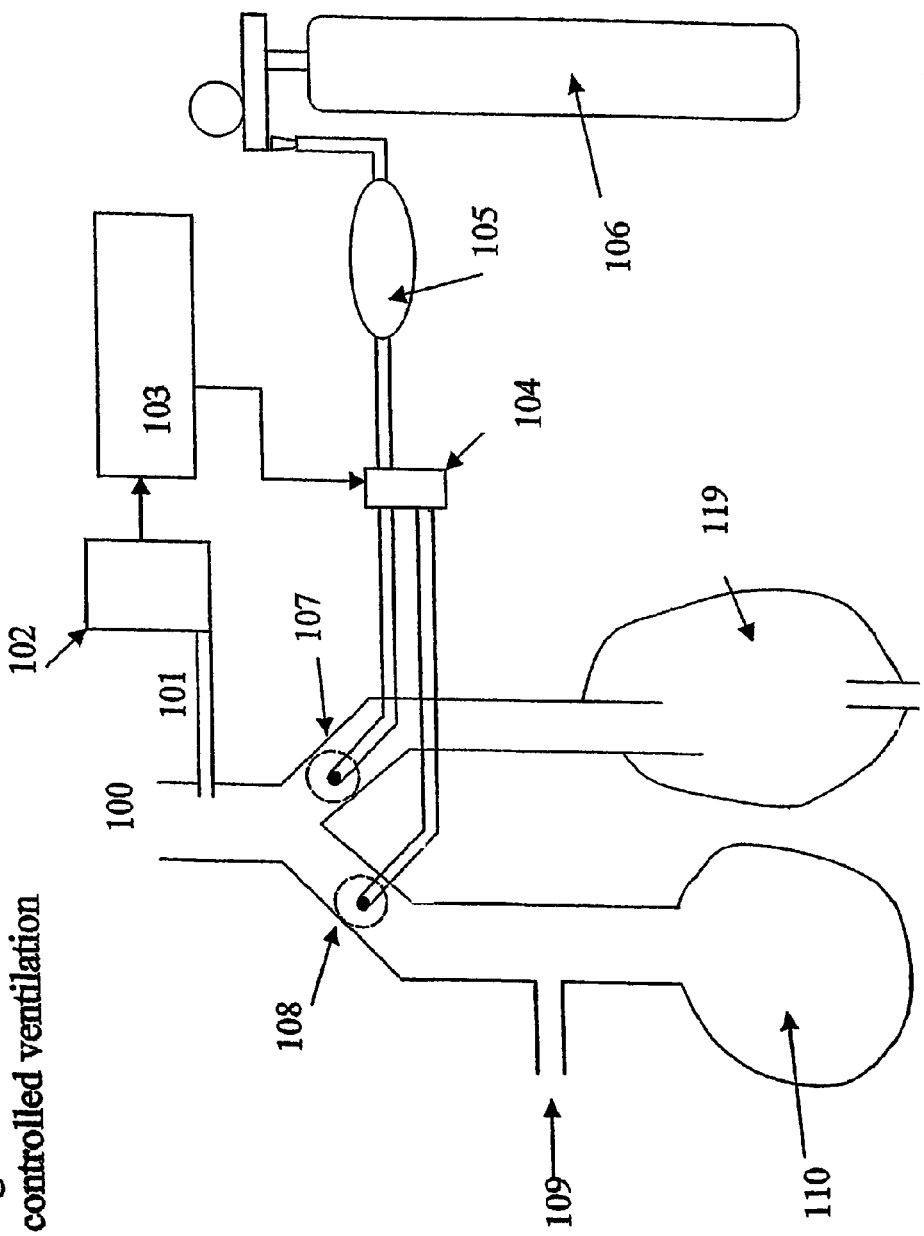

Figure 6. Schematic diagram of actively controlled rebreathing circuit for controlled ventilation

* Logic board algorithm: 1. positive pressure, balloon deflated. 2. Next negative pressure--> inflate balloon. 3. Next pressure <-2 cm H2O ->deflate balloon. 4. Next positive pressure, reset to 1. Note: one way valve can be replaced by second balloon valve that is inflated in 1, deflates in 2 and inflates in 3, making the method potentially even more accurate.

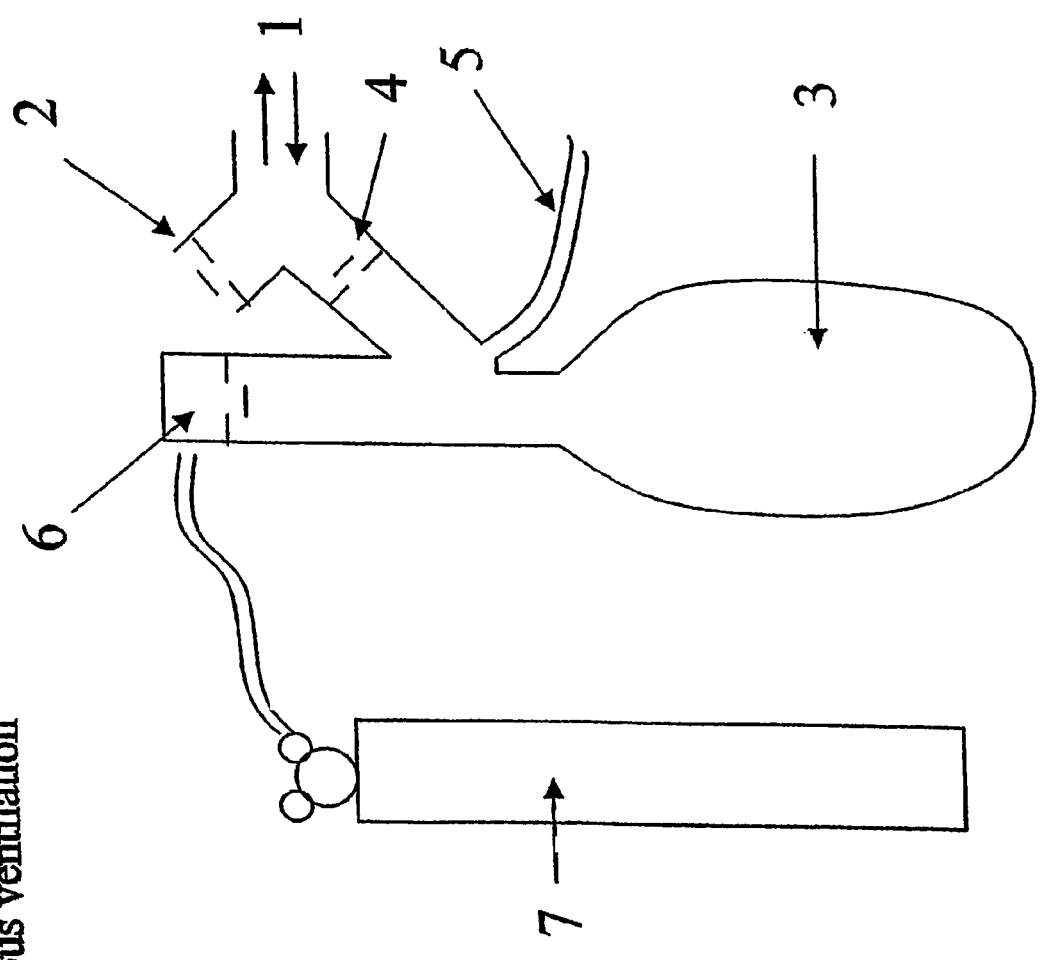
Figure 7. Schematic diagram of non-rebreathing isocapnia circuit for spontaneous ventilation

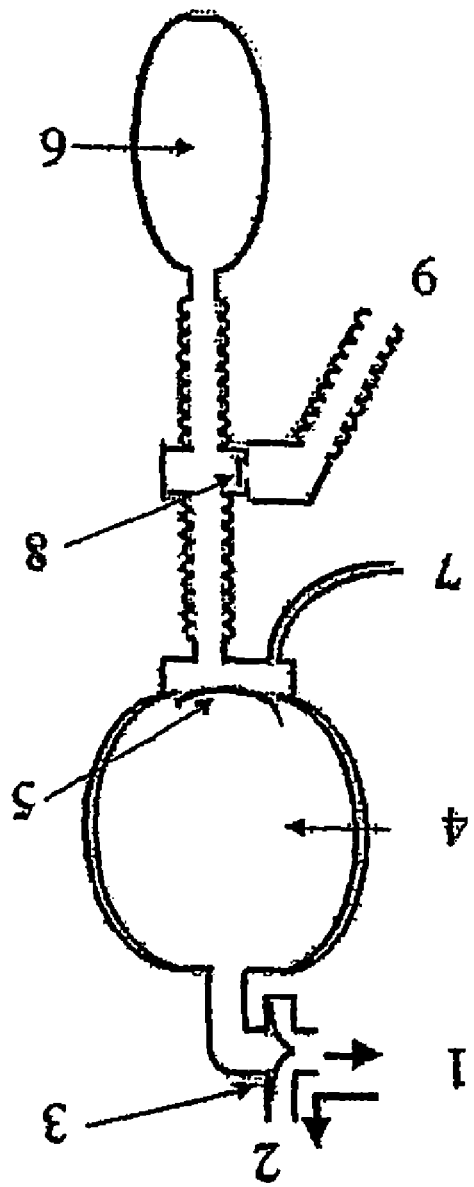
Figure 8. Schematic diagram of non-rebreathing isocapnia circuit for controlled ventilation Figure showing the 95% confidence intervals of our new method for measuring $V_{CO_2}$. X-axis shows average $V_{CO_2}$ or (Douglas bag $V_{CO_2}$ + new method) / 2
Y-axis shows deviation of new method from Douglas bag collection.

Figure showing progressive measurements of $V_{CO_2}$ using the standard bag collection, our new method, and a metabolic cart. Note the consistency of the new method compared to that of the others.

METHOD FOR CONTINUOUS MEASUREMENT OF FLUX OF GASES IN THE LUNGS DURING BREATHING

FIELD OF INVENTION

This invention relates to a method of measuring uptake and elimination via the lung of all gases for example including, but not limited to, anesthetics, oxygen and carbon dioxide.

BACKGROUND OF THE INVENTION

The following represents a glossary of terms used within the specification. The reader is referred to these definitions when interpreting the meaning of any description herein.
1) $\dot{V}_E$: minute ventilation (the total volume of gas breathed in and out of the lung per minute). $P_{ET}CO_2$: end tidal $PCO_2$ (the partial pressure of $CO_2$ at end exhalation);
2) SGF: source gas flow (the flow of gas into a breathing circuit, in liters/min);
3) $\dot{V}_A$: alveolar ventilation (that ventilation that results in gas exchange between the pulmonary capillaries and the air spaces (alveoli) of the lung), expressed in liters/min. It is also defined as the total ventilation minus the ventilation of the anatomic dead space ($\dot{V}_E - \dot{V}_{Dan}$);
4) $\dot{V}O_2$: The $O_2$ consumed in liters per minute;
5) $\dot{V}CO_2$: The $CO_2$ produced in liters per minute;
6) $F_{sx}$: fractional concentration of a gas x in source gas (gas entering a breathing circuit);
7) $F_{Ix}$: fractional concentration of gas x in inspired gas (gas entering the patient's lungs);
8) $F_{Ex}$: the fractional concentration of gas x in end expired gas;
9) CBC (conditional breathing circuit): a breathing circuit in which only exhaled gas, and no source gas, exits from the circuit, as would be the case with a circle circuit with a low flow of gas entering the circuit, or a Magill circuit in which a) SGF is $\leq 0.7 \times \dot{V}_E$; b) the common breathing tube volume (see FIG. 1) is greater than or equal to the sum of [(SGF× expiratory time)+the anatomical dead space]; c) the volume of the breathing bag is greater than [the largest expected tidal volume−(SGF×inspiratory time)].

Introduction

The measurement of uptake and elimination of gases via the lungs plays an important role in medicine. Oxygen consumption ($\dot{V}O_2$) and $CO_2$ production ($\dot{V}CO_2$) are two important parameters indicating cardio-respiratory fitness of athletes. $\dot{V}O_2$ and $\dot{V}CO_2$ are also used as important indicators of the efficacy of therapeutic intervention in critically ill patients. The ability to impose a transient change in $\dot{V}O_2$ and $\dot{V}CO_2$ allows one to calculate such important physiological parameters as cardiac output and functional residual capacity. For the most part, anesthesia is induced and maintained by gases taken up by and eliminated from the body via the lungs. Accurate measurement and control of uptake and elimination of anesthetic gases would improve the control of anesthetic depth and thereby the effectiveness and efficiency of the use of anesthetic gases. Accurate control of uptake and elimination of therapeutic gases would allow more controlled dosing when these gases are used as therapies for illness. Accurate control of uptake and elimination of inert gases via the lung can be used for various diagnostic and research purposes.

Present Art

Measuring Gas Flux

Measuring total gas flux requires the measurement of gas volumes for discrete periods of time and multiplying these volumes by the concentration of the gas in the volume.

Volume Measurements

Measurement of exhaled gas volumes is very cumbersome in clinical or research settings. One method requires timed collections of exhaled gas in bags and then measuring the volume of the bags. Inhaled volumes are even more awkward to measure continuously as the volumes enter the lung and one must measure the volume of lung expansion or the volume depleted from a previously known volume. This cannot be done breath-by-breath. These measurements are usually simplified by measuring flow continuously at the mouth and integrating the flow electronically with respect to time to obtain "continuous" measures of volume. Each type of flow measuring device has inherent problems leading to inaccuracy of calculation of volume (see below).

Flux Measurements

To measure the flux of a particular constituent (gas x) of the total gas that enters or exits the lung is more complex. The concentration of x sampled at the mouth during breathing changes between inhalation and exhalation as well as continuously during each ventilatory phase. Therefore, to measure the flux of gas x, the concentration of gas x must be measured continuously with a rapidly responding gas analyzer, and the average concentrations over short intervals must be multiplied by the volume changes over those same intervals. This requires synchronization of flow-volume signals and gas concentration signals, then multiplying the values and continuously summing them. A number of devices on the market such as the Vmax (Sensormedics, Yorba Linda Calif.), Medical Graphics CPOX/D, (Medical Graphics Corporation, St. Paul, Minn.) and NICO (Novametrix, Wallingford, Conn.) measure the fluxes of $CO_2$ and/or $O_2$ at the mouth using this method. The same principles apply to measuring the flux of other gases if appropriate gas sensors are used.

Measuring Gas Fluxes During Anesthesia a) Understanding the Anesthetic Circuits

One circuit used for anesthesia is the Magill circuit with the Mapleson A configuration illustrated in FIG. 1 ("Magill circuit"). The patient breathes through the patient port (30). During inhalation, gas is drawn from the source gas port (33) and the gas reservoir bag (34) along the common breathing tube (32). Expiration is divided into two phases. The first phase lasts from the beginning of exhalation until the filling of the gas reservoir bag (34). During this first phase of exhalation, expired gas proceeds down the common breathing tube (32) with gas from the anatomical dead space preceding gas from the alveoli. Expired gas displaces gas in the breathing tube (32) into the gas reservoir bag. During his phase of exhalation the source gas is also directed into the gas reservoir bag. The second phase of exhalation is from the time of filling of the gas reservoir bag (34) until the beginning of inhalation. During this second phase of exhalation, the expired gas exits through the one way pressure relief valve (31) that has an opening pressure of about 2 cm $H_2O$ and the source gas proceeds along the common breathing tube (32) displacing gas before it and forcing it out of the pressure relief valve such that the last exhaled (alveolar gas) exits the valve first.

Kain and Nunn (Kain M. L., Nunn J. F. *Anesthesiology.* 29: 964-974, 1968) determined the minimum source gas flow required to prevent rebreathing in anesthetized patients breathing through the circuit by sequentially decreasing the source gas flow until minute ventilation and end tidal $PCO_2$ increased. It is generally accepted that the source gas flow needed to prevent rebreathing of alveolar gas is 70% of the minute ventilation ($\dot{V}_E$) (Understanding Anesthesia Equipment by Dorsch J. A., and Dorsch S. E., Williams & Wilkins Co. 1975, pg. 169). The 30% savings in source gas is due to the rebreathing of the anatomical dead space gas which does not undergo gas exchange in the alveoli and therefore retains the same composition as source gas.

The 30% savings in source gas flow with the Magill breathing circuit represents the maximum efficiency available for source gas without the use of a $CO_2$ absorber. As the cost of anesthesia varies directly with the flow of source gas, circuits with $CO_2$ absorbers, the most popular being the "circle circuit" depicted in FIG. 2, allows a marked reduction in source gas flow (SGF) without causing a rise in end tidal $PCO_2$. The balance of $\dot{V}_E$ is provided by rebreathing of previously exhaled gases and the $CO_2$ absorber (6) prevents the build-up of $CO_2$ in the circuit and the patient. As not all of the delivered anesthetic is extracted during a breath, exhaled gas has a considerable concentration of anesthetic that can be re-supplied to the patient when rebreathed. The circle circuit contains a patient port (1), and an expiratory limb (2) leading to a one way expiratory valve (3). Distal to the valve there is a flexible gas reservoir (4), a pressure relief valve (5) where excess expired gas is vented, and a container for $CO_2$-absorbing crystals (6). When the patient inhales, he draws fresh gas entering the fresh gas inlet (7) and makes up the balance of inspired gas by drawing gas from the gas reservoir through the $CO_2$-absorber. The source gas and the previously exhaled gas join to flow through the one-way inspiratory valve (8) to the patient through the inspiratory limb (9). When the patient exhales, gas passes down the expiratory limb of the circuit (2), past the expiratory valve (3), and enters the flexible gas reservoir (4). When the gas reservoir fills to capacity, pressure in the circuit increases and the pressure relief valve (5) opens, releasing gas to atmosphere during the remainder of exhalation. During exhalation, fresh gas entering the circuit (7) is displaced back into the $CO_2$ absorber (6). This fresh gas enters the inspiratory limb (9) and is made available to the patient on subsequent breath(s).

The depletion of $O_2$ and anesthetic from the circuit is prevented by re-supplying both gases through the fresh gas inlet (7). The anesthesiologist can control the total flow of gas as well as the concentrations of all its constituent components such as oxygen, nitrous oxide and anesthetic agent. The minimum gas flow into the circuit is that needed to replace the oxygen consumed and anesthetic absorbed by the body. The $CO_2$ absorbers extract only $CO_2$, allowing other gases to pass through unchanged.

b) Calculation of Uptake or Elimination of Gases with Rebreathing Circuits (Present Art):

When a subject breathes via a Magill, circle, or Fisher isocapnia (rebreathing and non-rebreathing) circuit, and the SGF entering the circuit is equal to or greater than $\dot{V}_E$, the circuit acts like a nonrebreathing circuit, i.e., inspired concentration of gas x is that of the SGP, i.e., Fsx. When SGF is less than $\dot{V}_E$, inspired gas is composed of both SGF and previously exhaled gas in the Magill, circle and Fisher rebreathing isocapnia circuit; and composed of SGF and reserve gas in the Fisher non-rebreathing isocapnia circuit. As a result, the concentration of x varies throughout inspiration in a complex way depending on $\dot{V}_E$, pattern of breathing, and SGF. To measure the inspired volume of x, inspiration must be broken up into small intervals during which the total volume must be multiplied by the average concentration of x; the resulting discrete volumes of x must be summed for the duration of inspiration. Similarly, to calculate the expired volume of x, continuous measurements of expired flows and expired concentrations of x are required. The net uptake or elimination of x over a given time is the algebraic sum of the inhaled and exhaled volumes of x during that time.

REFERENCE LIST

1. Kain M L, Nunn J F. Fresh gas economics of the Magill Circuit. Anesthesiology 1968; 29(5):964-74.
2. Wissing H. Kuhn I, Rietbrock S, Fuhr U. Pharmacokinetics of inhaled anesthetics in a clinical setting: comparison of desflurane, isoflurane and sevoflurane [see comments]. Br. J Anaesth. 2000; 84(4):443-9.
3. Rietbrock S, Wissing H, Kuhn I, Fuhr U. Pharmacokinetics of inhaled anesthetics in a clinical setting: description of a novel method based on routine monitoring data [see comments]. Br. J Anaesth. 2000; 84(4):437-42.
4. Bouillon T, Shafer S L. Hot air or full steam ahead? An empirical pharmacokinetic model of potent inhalational agents [editorial; comment] [published erratum appears in Br J Anaesth 2000 June;84(6):833]. Br. J Anaesth. 2000; 84(4):429-31.

It is an object of this invention is to provide a simpler and more accurate method of measuring uptake and elimination via the lung of all gases for example including, but not limited to, anesthetics, oxygen and carbon dioxide.

It is a further object of this invention is to provide a method of controlling gas flux (defined as uptake or elimination from the lung) independent of minute ventilation.

Further and other objects of the invention will become apparent to those skilled in the art when considering the following summary of the invention and the more detailed description of the preferred embodiments illustrated herein.

SUMMARY OF THE INVENTION

According to a primary aspect of the invention we provide a method of measuring the flux of any gas by utilizing SGF times expired concentration of that gas. This is especially applicable in the operating room where all of the equipment required to provide the necessary information is already in use: the circuit, the SGP flowmeters, the gas sensors.

The ability to make a step change in $\dot{V}_A$ via a change in SGF or Fsx can be used to obtain a control measurement of $\dot{V}_A$ as well as cardiac output by two different methods, the Gideon method and the Fisher method. This proffers marked advantages on these methods with respect to versatility, cost, and accuracy.

The method relates to the novel application of known circuits for measurements of gas flux. Further three new circuits that allow the use of the method outside the operating room in ventilated patients/subjects are also provided, a) the Magill configured for controlled ventilation; b) the rebreathing isocapnia circuit configured for controlled ventilation; and c) the balloon valve circuit.

With reference to the gas input the following conditions apply/result:

Breathing via a circuit in which the total flow of gas entering the circuit is less than or equal to the subject's alveolar ventilation, The balance of gas inhaled is composed of gas that has substantially the same concentration of gas x as is in the alveoli of the lung This gas may actually be previously exhaled gas that has been stored and made available to be rebreathed, or it may come from an external gas source in which the concentration of x is substantially the same as that in the alveoli of the lung The input gas flow and concentration of x in input gas are known and determined by the user The continuous measurement of expired gas concentrations is possible by utilizing a convenient gas analyzer. Based on the known values therefore that will be further described herein after;

The rate of elimination of gas $x=SGF \times (F_{EX}-F_{SX})$ for any CBC circuit as described herein.

The rate of elimination of gas x = the input total gas flow × ($F_{EX}$−$F_{IX}$), where $F_{IX}$ is the concentration of x in inspired gas Gas input parameters Breathing via a circuit in which the total flow of gas entering the circuit is less than or equal to the subject's alveolar ventilation, The balance of gas inhaled is composed of gas that has substantially the same concentration of gas x as is in the alveoli of the lung This gas may actually be previously exhaled gas that has been stored and made available to be rebreathed, or it may come from an external gas source in which the concentration of x is substantially the same as that in the alveoli of the lung The input gas flow and concentration of x in input gas are known and determined by the user According to one aspect of the invention there is provided a method of calculating the flux of any gas(x) in a CBC circuit for a ventilated or a spontaneous breathing subject,
  for example said gas(x) being;
  a) an anesthetic such as but limited to;
    i) $N_2O$;
    ii) sevoflurane;
    iii) isoflurane;
    iv) halothane;
    v) desflurame;
    or the like
  b) Oxygen;
  c) Carbon dioxide;
  or the like
  utilizing the following relationships;

$$\text{Flux of gas}(x) = SGF(F_{SX} - F_{EX})$$

wherein
  SGF=Source of gas flow into the breathing circuit (CBC circuit) in liters/minute as read from the gas flow meter as set by the anesthesiologist;
  $F_{SX}$=Fractional concentration of gas X in the source gas (which is set by the anesthesiologist);
  $F_{EX}$=Fractional concentration of gas X in the end expired gas as determined by a portable gas analyzer, or the like.

According to another aspect of the invention there is also provided a method of calculating the flux of oxygen in a CBC circuit for a ventilated and/or spontaneous breathing subject utilizing the following relationship;

$$\text{Flux of oxygen} = SGF(F_{SO2} - F_{EO2})$$

wherein
  SGF=Source of gas flow into the breathing circuit (CBC circuit) in liters/minute as read from the gas flow meter as set by the anesthesiologist;
  $F_{SX}$=Fractional concentration of gas $O_2$ in the source gas (which is set by the anesthesiologist);
  $F_{EX}$=Fractional concentration of gas $O_2$ in the end expired gas as determined by a portable gas analyzer, or the like.

In one embodiment for the abovementioned methods the CBC circuit is selected from the group consisting of i) a circle circuit; ii) a Magill breathing circuit; iii) an isocapnia circuit, whether breathing or non-breathing (as taught by co-pending Fisher et al), or the like.

In another embodiment for the abovementioned methods the CBC circuit is an improved Magill circuit as described herein.

In yet another embodiment for the abovementioned methods the CBC circuit is an improved rebreathing circuit as described herein.

In yet another embodiment for the abovementioned methods the CBC circuit is an improved non-rebreathing circuit as described herein.

Preferably in yet another embodiment the abovementioned methods are used to determine oxygen consumption in order to measure cardiac out put by any known method, such as the Fick method.

Preferably in yet another embodiment the abovementioned methods are used to determine oxygen consumption in, for example, an operating room setting or the like. Preferably in yet another embodiment the abovementioned methods are used to optimize oxygen consumption. Preferably the abovementioned methods are utilized as an early indication of malignant hyperthermia.

According to yet another aspect of the invention there is provided a method of calculating the flux of any gas other than carbon dioxide, in a CBC circuit with low gas flow of source gas and with a carbon dioxide absorber in place utilizing the following relationship;

$$\text{Flux of gas } X = SGF(F_{EX} - F_{RBX})$$

wherein
  SGF=Source of gas flow into the breathing circuit (CBC circuit) in liters/minute as read from the gas flow meter as set by the anesthesiologist;
  $F_{EX}$=Fractional concentration of gas X in the end expired gas as determined by a portable gas analyzer, or the like;
  $F_{RBX}$=Concentration of gas X in the expired limb of circuit before the gas passes through the carbon dioxide absorber and mixes with gas coming from the flow meter.

Preferably in yet another embodiment the abovementioned methods are used to determine the flux of an anesthetic for example:
  i) $N_2O$;
  ii) sevoflurane;
  iii) isoflurane;
  iv) halothane;
  v) desflurame,
  or the like Preferably said methods are used to determine how much anesthetic is being absorbed by the patient. Preferably said anesthetic is $N_2O$.

According to yet another aspect of the invention there is provided an improved Magill circuit the improvement comprising an inspiratory and expiratory limbs, a pressure relief valve at the end of the expiratory limb, a port for entry of SGF, and a gas reservoir bag, the components of the Magill system utilized for spontaneous ventilation; or alternatively for controlled ventilation, the gas reservoir bag is enclosed in a container with a port for connection to a ventilator breathing circuit, the pressure relief valve being enclosed in a container with a port for connection to a ventilator breathing circuit;
  wherein on exhalation, the patient breathes out through the patient port and during the initial part of exhalation, the gas reservoir is partially empty and the resistance to flow along the inspiratory limb is less than that of the expiratory limb because the higher opening pressure of the pressure relief valve must be overcome before flow can proceed through the expiratory limb,
  wherein during the initial part of expiration, the expired gas enters the inspiratory limb, displacing gas in the inspiratory limb and from the SGF into the gas reservoir, as the gas reservoir fills, the pressure in the circuit increases above the opening pressure of the pressure relief valve and the remainder of the expired gas is directed down the expired limb displacing the gas out of the expired limb through the pressure relief valve to the ventilator breathing circuit from where it is eventually vented to atmosphere through the expiratory port and the SGF continues to flow towards the patient down the inspiratory limb, displacing previously exhaled gas into the expiratory limb;

wherein during inhalation, the balloon valve occludes the ventilator circuit expiratory port and a volume of gas equal to a tidal volume is delivered by the ventilator into the ventilator circuit and hence into the SGF gas reservoir box, thereby displacing a volume equal to the tidal volume from the SGF gas reservoir into the inspiratory limb of the Magill circuit, the SGF continues to flow towards the patient down the inspiratory limb;

wherein the net tidal volume of the patient is equal to the volume displaced from the gas reservoir plus the SGF multiplied by the duration of inspiration, because the pressures on both sides of the Magill pressure relief valve are equal during inspiration, the differential pressure provided by the "opening pressure" of the valve keeps it dosed during inspiration;

assuming that:
  (1) the volume of the inspiratory limb is greater than or equal to [(SGF×expiratory time)+the anatomical dead space]; and the breathing bag volume is greater than [the largest expected tidal volume−(SGF×inspiratory time)],
  (2) SGF is $\leq 0.7 \times \dot{V}_E$ According to yet another aspect of the invention there is provided an improved rebreathing isocapnia circuit comprising a Y piece with a patient port, and inspiratory limb of the Y piece with a one way inspiratory valve and an expiratory limb of the Y piece with a one way expiratory valve; the inspiratory limb being connected to a SGP and a gas reservoir, the expiratory limb leading to an expiratory gas reservoir, the expiratory gas reservoir having a one way valve at the port where expired gases are vented from the expired gas reservoir which allows gas to exit the expiratory gas reservoir but not enter, having disposed between the expiratory limb and the inspiratory limb distal to the inspiratory and expiratory valves a bypass limb that contains a one-way valve with an opening pressure of the valve, being for example approximately 1.5 cm H₂O, greater than the valves in the inspiratory limb of the Y piece and the expiratory limb of the Y piece; the direction of opening of the one-way valve in the bypass limb being from the expiratory limb to the inspiratory limb, the inspiratory and expiratory limbs being extended by tubing of variable lengths, the inspiratory and expiratory reservoirs being enclosed in a box with 3 ports; one port communicates with the box, one port communicates with the interior of the SGF reservoir only, one port communicates with the expiratory gas reservoir, the SGF reservoir is continuous with the inspiratory limb of the circuit, the expiratory gas reservoir is continuous with the expiratory limb of the circuit and has a port through which expired gas exits the expired gas reservoir and enters the box, a ventilator, a mushroom valve synchronized to occlude the ventilator circuit expiratory port during the inspiratory phase attached to the box ventilator port such that during the inspiratory phase, the tidal volume of the ventilator is discharged into the box, which will displace an equal volume from the gas reservoirs in the box; as the valve in the bypass limb has a greater opening pressure than the inspiratory valve, the inspiratory reservoir will be compressed in preference to the expiratory reservoir, when the inspiratory reservoir is collapsed, the remainder of the tidal volume will result from compression of the expiratory reservoir and displacement of gas through the bypass limb and valve and inspiratory valve to the patient, the total tidal volume will be equal to the volume displaced from the inspiratory reservoir plus the volume displaced from the expiratory reservoir plus the SGF multiplied by the time during inspiration; during exhalation, the balloon valve is deflated, opening the expiratory port of the ventilator circuit to atmosphere and the expiratory reservoir bag to atmosphere via the port, thus allowing exhaled gas to flow past the expiratory one-way valve down the expiratory lid into the expiratory reservoir, SGF flowing into the port being directed down the inspiratory limb to the SGP reservoir, wherein gas is displaced in the box by expansion of the SGF reservoir and the expiratory gas reservoir is displaced from the box via the ventilator expiratory port; wherein SGF is less than or equal to $\dot{V}_E - \dot{V}_{Dan}$.

According to yet another aspect of the invention there is provided an improved non-rebreathing circuit, the improvement comprising a balloon valve circuit for spontaneous ventilation of a patient breathing spontaneously, said circuit having a Y piece with a patient port, an inspiratory limb including a balloon valve, connected to SGF and a gas reservoir, an expiratory limb consisting of a balloon valve leading to an expiratory gas reservoir, which has a port opening to the atmosphere, a tank of compressed air flows through solenoid valves to open or close the balloon valves, the solenoid valves being controlled electronically by a computer, a pressure transducer connected to a mouthpiece for measuring when the fresh gas reservoir has been fully collapsed, the computer for receiving the signal and sending a signal to the solenoid valve to dose the inspiratory valve and open the expiratory valve, the fresh gas flow continuously filling the fresh gas reservoir.

Preferably any previous method described herein may be used to calculate the rate of elimination of a gas X for any input total gas flow utilizing the following further relationships;

wherein the rate of elimination of gas X=the input total gas flow (multiplied by) $F_{EX}-FI_X$;
  wherein $F_{EX}$ is defined above and $F_{IS}$ is the concentration of X in inspired gas.

Preferably said method is incorporated in an algorithm spreadsheet, formula or the like contained within software which is capable of running on a computing device, or is installed therein.

BRIEF DESCRIPTION OF THE DRAWINGS

In the following examples, there are described several preferred embodiments to illustrate the invention. However, it should be understood that the invention is not intended to be limited to the specific embodiments.

FIG. 1 is schematic diagram of a typical Magill circuit having a Mapleson A configuration.

FIG. 2 is schematic diagram of a typical circle anesthetic circuit.

FIG. 3 is schematic diagram of an improved Magill circuit having a Mapleson A configuration for controlled ventilation illustrated in one embodiment of the invention FIG. 4 is schematic diagram of an improved rebreathing isocapnia circuit for spontaneous ventilation illustrated in one embodiment of the invention.

FIG. 5 is schematic diagram of an improved rebreathing isocapnia circuit for controlled ventilation illustrated in one embodiment of the invention.

FIG. 6 is schematic diagram of an an actively controlled rebreathing circuit for controlled ventilation illustrated in one embodiment of the invention.

FIG. 7 is schematic diagram of a non-rebreathing isocapnia circuit for spontaneous ventilation illustrated in one embodiment of the invention.

FIG. 8 is schematic diagram of a non-rebreathing isocapnia circuit for controlled ventilation illustrated in one embodiment of the invention.

DETAILED DESCRIPTION OF EMBODIMENTS OF THE INVENTION

Figure 9A:
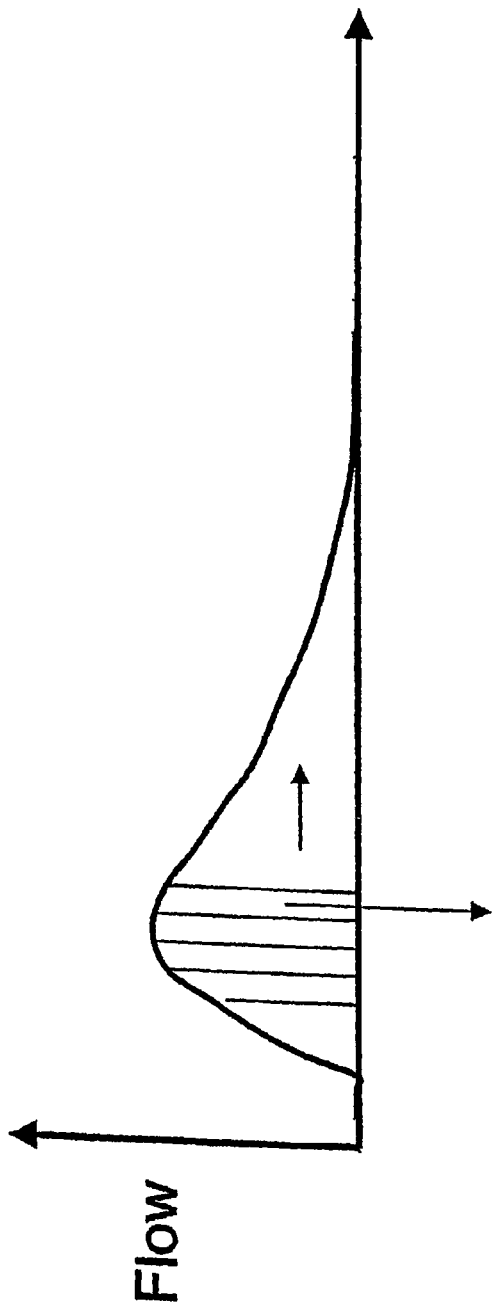
FIGS. 9A and 9B illustrate diagrams of flow and integrated concentration curves for carbon dioxide.

The reader is referred generally to the figures with regard to the following description of various embodiments of the invention.

Our Improved Method:

Circuit:
- a) A rebreathing circuit in which only exhaled gas and no source gas exits from the circuit, as would be the case with
  - i) a circle circuit,
    - (1) patient breathing spontaneously or mechanically ventilated,
    - (2) SGF much less than $\dot{V}_E$, for example SGP is less than half of $\dot{V}_E$,
  - ii) Magill circuit
    - (1) Patient breathing spontaneously
    - (2) Ventilated patients: The Magill circuit (FIG. 1) was designed for spontaneously breathing patients only as it was felt that the efficiencies of the circuit vis a vis conservation of SGF could not be obtained with manual-assisted or mechanical ventilation (1). We describe a modification of the Magill breathing circuit that will provide all of the benefits with respect to calculation of gas flux during mechanical ventilation. The circuit (FIG. 3) consists of a Y-piece (47) with an opening to the patient (35) and inspiratory (38) and expiratory (36) limbs, a pressure relief valve at the end of the expiratory limb (37), a port for entry of SGF (39), and a gas reservoir bag (40)—components of the Magill system used for spontaneous ventilation. For controlled ventilation, the gas reservoir bag (40) is enclosed in a container with a port (44) for connection to a ventilator breathing circuit. The pressure relief valve (37) is enclosed in a container (48) with a port for connection to a ventilator breathing circuit.

On exhalation, the patient breathes out through the patient port (35). During the initial part of exhalation, the gas reservoir (40) is partially empty and the resistance to flow along the inspiratory limb (38) is less than that of the expiratory limb (36) because the higher opening pressure of the pressure relief valve (37) must be overcome before flow can proceed through the expiratory limb (36). Therefore, during the initial part of expiration, the expired gas enters the inspiratory limb (38), displacing gas in the inspiratory limb (38) and from the SGF (39) into the gas reservoir (40). When the gas reservoir (40) fills, the pressure in the circuit increases above the opening pressure of the pressure relief valve (37) and the remainder of the expired gas is directed down the expired limb (36) displacing the gas out of the expired limb through the pressure relief valve (37) to the ventilator breathing circuit from where it is eventually vented to atmosphere through the expiratory port (49). The SGF continues to flow towards the patient down the inspiratory limb (38), displacing previously exhaled gas into the expiratory limb (36).

During inhalation, the balloon valve (43) occludes the ventilator circuit expiratory port (49) and a volume of gas equal to a tidal volume is delivered by the ventilator (42) into the ventilator circuit (46) and hence into the SGF gas reservoir box (41), thereby displacing a volume equal to the tidal volume from the SGP gas reservoir (40) into the inspiratory limb of the Magill circuit (38). The SGF continues to flow towards the patient down the inspiratory limb (38). The net tidal volume of the patient is equal to the volume displaced from the gas reservoir (40) plus the SGF multiplied by the duration of inspiration. Because the pressures on both sides of the Magill pressure relief valve (37) are equal during inspiration, the differential pressure provided by the "opening pressure" of the valve (37) keeps it closed during inspiration.
    - (3) the volume of the inspiratory limb is greater than or equal to [(SGF×expiratory time)+the anatomical dead space]; the breathing bag volume is greater than [the largest expected tidal volume−(SGF×inspiratory time)],
    - (4) SGF is $\leq 0.7 \times \dot{V}_E$
  - iii) The rebreathing isocapnia circuit:
    - (1) Patient breathing spontaneously (Fisher rebreathing isocapnia circuit, FIG. 4). Circuit consists of a Y piece with patient port (58), and inspiratory limb of Y piece (60) with a one way inspiratory valve (59) and an expiratory limb of Y piece (61) with a one way expiratory valve (53). The inspiratory limb is connected to SGF (51) and a gas reservoir (52). The expiratory limb leads to an expiratory gas reservoir (56). The expiratory gas reservoir (56) has a port opening to atmosphere (57). Between the expiratory limb and the inspiratory limb, distal to the inspiratory (59) and expiratory (53) valves, is a bypass limb (62) that contains a one-way valve (54) with an opening pressure approximately 1.5 cm $H_2O$ greater than the inspiratory (53) and expiratory (59)valves; the direction of opening of the one-way valve in the bypass limb (62) is from expiratory limb to the inspiratory limb.
    - (2) Patient ventilated: The rebreathing isocapnia circuit was described for spontaneously breathing subjects, and its use with ventilated subjects was not contemplated. Accordingly, to use the circuit for controlling $\dot{V}_A$ and measuring gas flux during controlled ventilation, we describe a new rebreathing isocapnia circuit suitable for use with mechanically ventilated subjects. Referring to FIG. 5: The circuit consists of a Y piece with patient port (58), and inspiratory limb of Y piece with a one way inspiratory valve (78) and an expiratory limb of Y piece with a one way expiratory valve (77). The inspiratory limb is connected to a SGF (66) and a gas reservoir (67). The expiratory limb leads to an expiratory gas reservoir (69). The expiratory gas reservoir (69) has a one way valve (81) at the port where expired gases are vented from the expired gas reservoir (71) which allows gas to exit the expiratory gas reservoir but not enter it. Between the expiratory limb and the inspiratory limb, distal to the inspiratory (78) and expiratory (77) valves is a bypass limb that contains a one-way valve (65) with an opening pressure of the valve approximately 1.5 cm $H_2O$ greater than valves in the inspiratory limb of the Y piece (78) and the expiratory limb of the Y piece (77); the direction of opening of the one-way valve in the bypass limb (65) is from the expiratory limb to the inspiratory limb. The inspiratory and expiratory limbs are extended by tubing of variable lengths, (64) and (72) respectively. The inspiratory (67) and expiratory (69) reservoirs are enclosed in a box with 3 ports: one port (79) communicates with the box; one port (80) communicates with the interior of the SGF reservoir only; one port (70) communicates with the expiratory gas reservoir. The SGF reservoir (67) is continuous with the inspiratory limb (64) of the circuit. The expiratory gas reservoir (69) is continuous with the expiratory limb of the circuit (72) and has a port (71) through which expired gas exits the expired gas reservoir and enters the box. A ventilator (73) a mushroom valve (74)synchronized to occlude the ventilator circuit expiratory port (75) during the inspiratory phase, is attached to the box ventilator port (79) such that, during the inspiratory phase, the tidal volume of the ventilator is discharged into the box (68). This will displace an equal volume from the gas reservoirs in the box. As the valve in the bypass limb (65) has a greater opening pressure than the inspiratory valve (78), the inspiratory reservoir (67) will be compressed in preference to the expiratory reservoir (69). When the inspiratory reservoir is collapsed, the remainder of the tidal volume will result from compression of the expiratory reservoir (69) and displacement of gas through the bypass limb and valve (65) and inspiratory valve (78) to the patient. The total tidal volume will be equal to the volume displaced from the inspiratory reservoir (67) plus the volume displaced from the expiratory reservoir (69) plus the SGF multiplied by the time during inspiration.

During exhalation, balloon valve (74) is deflated, opening the expiratory port of the ventilator circuit (75) to atmosphere and the expiratory reservoir bag to atmosphere via port (71), thus allowing exhaled gas to flow past the expiratory one-way valve (77) down the expiratory limb (72) into the expiratory reservoir (69). SGF flowing into port (66) is directed down the inspiratory limb (64) to the SGF reservoir (67). Gas displaced in the box (68) by expansion of the SGF reservoir (67) and the expiratory gas reservoir (69) is displaced from the box via the ventilator expiratory port (75).

(4) SGF is less than or equal to $\dot{V}_E - \dot{V}_{Dan}$.

iv) Non-rebreathing isocapnia circuit:
(1) Spontaneous ventilation (as per Fisher patent, see FIG. 7) The subject breathes in and out through port (1). Upon expiration one way valve (2) opens and allows expired gas to leave the circuit. Simultaneously, one way valve (4) is forced shut and allows fresh gas reservoir (3) to fill up with pressurized gas from gas source (5). Upon inhalation, one way valve (2) is forced closed and one way valve (4) is opened, drawing in fresh gas stored in the reservoir (3). If the volume in the reservoir is insufficient for a single tidal volume, the residual volume of the breath is drawn from demand valve (6), connected to a pressurized gas source of $CO_2$. The preferred concentration of this gas source is arterial $PCO_2$ to maintain isocapnia.

(2) Controlled ventilation (as in dog paper with Laerdal bag, see FIG. 8)
During controlled ventilation the subject breathes through port (1). Non-rebreathing valve (3) forces expired gas through port (2). During inspiration gas is inspired from the self inflating bag (4) using a mechanical force to drive the gas through non-rebreathing valve (3). One way valve (5) ensures that all the gas within the bag is forced through valve (3) only. Simultaneously, fresh gas from pressurized source (7) fills up the fresh gas reservoir (6).
During expiration the bag is allowed to self-inflate with gas stored in fresh gas reservoir. If the volume stored in the reservoir is insufficient for a single tidal volume, the residual volume of the bag is made up of gas drawn through low pressure valve (8) from a pressurized source (9), ideally containing arterial concentrations of $CO_2$ to maintain isocapnia.

iii) Balloon valve circuit
(1) Spontaneous ventilation (see FIG. 6)
Patient breathing spontaneously (balloon isocapnia circuit, FIG. 6). Circuit consists of a Y piece with patient port (100). Inspiratory limb consists of a balloon valve (108), connected to SGF (109) and a gas reservoir (110). Expiratory limb consists of a balloon valve (107), leads to an expiratory gas reservoir (119), which has a port opening to the atmosphere. A tank of compressed air (106) flows through solenoid valves (104) to open or close balloon valves (108 and 107). The solenoid valves are controlled electronically by a computer (103).
A pressure transducer (102) connected to the mouthpiece (101) measures when the fresh gas reservoir has been fully collapsed. A computer receiving the signal (103) sends a signal to solenoid valve (104) to dose inspiratory valve (108) and open expiratory valve (107). The fresh gas flow (109) continuously fills fresh gas reservoir (110).

Henceforth, all of the above circuits, under conditions suitable for measuring flux of gas using SGP, Fsx, and Fex will be referred to collectively as "conditionalbreathingcircuits,orCBC".

For all CBC, we calculate the flux of gas x by multiplying SGF (as read from the gas flow meter as set by the anesthesiologist) by the difference between the expired gas concentration of x (Fex) and the gas concentration of x being delivered into the circuit (Fsx) (which is also set by the anesthesiologist). Thus, for any gas x (other than $CO_2$ if a circle anesthetic circuit contains a $CO_2$ absorber in the circuit, see below):

$$\text{Flux of gas } x = SGF(F_{Sx} - F_{Ex}) \tag{1}$$

The advantage of using equation (1) to calculate flux, is that a) SGF is set by the anesthesiologist, is precisely known, and is constant; b) Fsx is set by the anesthesiologist and is precisely known and is constant. This contrasts with the inspired concentration measured at the mouth, $F_{IX}$, which may vary throughout inspiration.

Rationale for New Approach:

The principle will be illustrated with a circle circuit (see FIG. 2), but similar considerations can be made for all of the circuits and conditions outlined below.

With a patient breathing via a circle circuit, and SGF set substantially lower than $\dot{V}_E$, for example one half $\dot{V}_E$, only exhaled gas leaves the circuit. Therefore, at low SGF, all of the SGF can be considered "fresh gas" and will contribute to alveolar ventilation. Therefore we consider SGF=$\dot{V}_A$. The rest of the gas entering the alveoli is rebreathed gas. Another way of looking at this is to consider the patient to be an additional gas compartment of the circuit; we can then consider the mass balance as it applies to the circuit alone. From the perspective of the circuit, we no longer need to deal with the complex gas concentrations and flows that occur at the circuit-patient interface as in the previous art. We deal only with the gas concentrations and flows that occur with respect to gases entering and leaving the circuit. The volume of a gas entering the circuit (SGF×$F_{SX}$) is equal to that of the gas eliminated from the circuit (SGF×$F_{EX}$) plus that of the gas absorbed or eliminated by the patient (SGF [$F_{SX}$–$F_{EX}$]).

In summary, our method can be stated as: volume of gas x entering or leaving a patient=volume of gas x entering the circuit−volume of gas x leaving the circuit=SGF×$F_{SX}$−SGF×$F_{EX}$ Or Flux of gas x=SGF($F_{SX}$−$F_{EX}$)

The prior art does not indicate that this is sufficient to calculate the uptake and elimination of gases during anesthesia and continues to require the flow-averaged concentrations of gas during inspiration and expiration measured at the patient-circuit interface, i.e., at the mouth of the patient, to calculate gas flux. This is evidenced by recent articles, for example by Wissig (2) and Rietbrock (3) which are accepted as reflecting the state of the art by an editorial in the British Journal of Anaesthesia by Bouillon and Shafer (4), the latter being recognized in the anesthesia profession as a world authority in the field of pharmacokinetics Advantages of our Approach Over Previous Methods:

The advantages of our method in calculating the flux of a gas x would apply with the use of any circuit in which the concentration of gas x in SGF entering the circuit is known, SGP is less than or equal to $\dot{V}_E$–$\dot{V}_{Dan}$ and the circuit is such that the difference between $\dot{V}_E$ and SGF is made up of reserve gas, the concentration of x in the reserve gas being substantially that in the alveoli at end exhalation; an example of reserve gas of suitable composition is previously exhaled gas. Examples of such circuits are the Magill circuit (Mapleson A configuration, referred to as the 'Magill circuit'), the circle anesthetic circuit, and the rebreathing and non rebreathing isocapnia circuit (Fisher patents).

The circle anesthetic circuit is the most commonly used circuit during anesthesia. All anesthetic machines allow precise setting of SGF and its composition. Therefore, SGF and Fsx are precisely known. Machines to continuously read out concentrations of such gases as $CO_2$, $O_2$, $N_2O$, and anesthetic vapors have been widely available for over a quarter of a century and are routinely available with all modern anesthetic systems. With our method, the flux of any gas x can be readily determined by multiplying SGP by ($F_{SX}$–$F_{EX}$). Oxygen and $CO_2$ analyzers are compact and readily available outside of the operating room. The Mapleson A circuit and the rebreathing isocapnia circuit (Fisher) are inexpensive, easy to assemble, and can be applied outside of the operating room. The method of measurement of gas flux can be applied to measuring $O_2$ consumption, $CO_2$ production, pharmacokinetics of inhaled anesthetics and other drugs, and cardiac output (the latter the subject of a separate patent application).

1) Measuring Alveolar Ventilation:

$\dot{V}_A(\dot{V}_E-\dot{V}_{Dan})$ is very difficult to measure for two reasons.

a) First, $\dot{V}_E$ is difficult to measure, To do this, one requires a device to measure flow such as a pneumotachometer and machine intelligence to integrate the flow signal with respect to time and calculate volume. Whereas minute ventilation can be calculated in mechanically ventilated subjects from ventilator settings, it must be, measured directly in spontaneously breathing subjects. All flow sensing devices have drawbacks:

i) Pneumotachometers based on pressure differentials are expensive and cumbersome to use outside a laboratory setting. They are affected by changes in gas temperature and composition; condensation from expired gas changes their calibration and requires addition of external heaters which introduces its own errors at high flow rates. They are also subject to drift, in part for the reasons just given, and require, or would benefit from, frequent recalibration.

ii) Electronic turbines use low resistance rotating vanes to measure volumes. Their major drawbacks include friction and inertia of the vane, resulting in a lag before flow is detected and continued spin after flow has ceased iii) Pitot tubes measure the pressure flowing against a series of small tubes mounted at 90 degrees to the direction of gas flow. They are notoriously alinear and sensitive to changes in gas composition, as occurs during breathing.

iv) Hot-wire (mass flow) anemometers rely on the cooling effect caused by laminar gas flow. However, they require sophisticated electronics and difficult calibrations to maintain accuracy.

b) Second, anatomical dead space, $\dot{V}_{Dan}$, is difficult to measure and estimates based on body weight are inaccurate. Measurement of anatomical dead space requires particular equipment and monitors and is prohibitively difficult to do outside of a specialized laboratory.

Our method: The alveolar ventilation can be known precisely by simply reading the flow setting on the flowmeter, which is a precisely calibrated instrument. Therefore, our method does not require the expense of pneumotachometers is not affected by the inaccuracies inherent in the use of pneumotachometers circumvents the complexity of measuring minute ventilation, integration of flow, and the requirement for precise rapid measures of gas concentrations (see below).

circumvents the complexity of measuring anatomical dead space, is just as accurate for spontaneously breathing subjects as it is with ventilated subjects.

2) The previous art requires that measurements of flow be synchronized with measurements of gas concentrations in order to calculate the breath-by-breath flux of gas. The inspired gas concentration while breathing on a rebreathing circuit varies continuously throughout the breath. The net inspired volume of gas x is a flow-weighted average of the inspired gas concentration. To be able to calculate this accurately, a very rapidly responding gas analyzer and precise synchronization to the flow signal are required. This is very difficult in a laboratory setting, and even more difficult in a clinical setting. At higher flows, small errors in synchronization will give large errors in gas flux. Each error is then multiplied by the number of breaths.

With our method, only the average expired concentration of gas is required. This allows the use of much less expensive and slower portable gas analyzers. During any testing procedure, gas concentrations in the gas mixture delivered to the circuit are set by the person doing the test. When breathing through a rebreathing circuit and when SGF limits $\dot{V}_A$, gas flux calculations are simplified to $SGF \times (F_{SX} - F_{EX})$.

3) The calculation with our method is more robust and accurate that that with the prior art (see data).

a) With our method, SGF, $F_{SX}$, and $F_{EX}$ are precisely known. With the prior art, the errors in measuring flow, gas concentrations, and synchronization of flow and concentration signals, are additive.

b) Our method is independent of $\dot{V}_E$ and extent of rebreathing. With the prior art, inaccuracy of measurement of gas flux increases as $\dot{V}_E$ and the extent of rebreathing increases.

Applications for Gas Flux Measurement:

1) Oxygen flux:

At present, there is no practical means to follow oxygen consumption intra- and post-operatively in the recovery room or intensive care area. Metabolic carts that perform this function require the additional means to measure gas flow and complex machine intelligence. Such machines typically cost in excess of US$25,000 each, making it prohibitively expensive for routine use.

Our method would allow continuous and intermittent measurements of oxygen consumption in ventilated as well as spontaneously breathing patients who are in the operating room. Outside of the operating room, any of the CBC described above can be used to calculate oxygen consumption by means of a simple calculation and without the cost of additional hardware.

a) In the Operating Room

Oxygen consumption is an important index of health. Optimization of oxygen consumption has been shown to decrease post-operative mortality and morbidity, and improve organ function and survival in patients undergoing intensive care after trauma, shock, sepsis and major surgery.

Increases in oxygen consumption would be a very sensitive early sign of malignant hyperthermia (MH), a rare but devastating condition triggered by anesthesia and consisting of sudden explosive hypermetabolism, increased oxygen consumption, $CO_2$ production, and high body temperature. Currently, all anesthetized patients are monitored with temperature probes. Increases in oxygen consumption would be a much earlier sign of MH than increases in body temperature. Early detection and thus early intervention would allow MH to be aborted before the fulminant stage, averting much morbidity and saving many lives. Furthermore, monitoring oxygen consumption with our method would be a much less expensive than with electronic temperature probes which are expensive and, because they have to be sterilized between patients, have short life spans.

Closed circuit anesthesia provides maximum efficiency of use of an anesthetic gas. At present, determining the $O_2$ flow for closed circuit anesthesia requires "trial and error" adjustments of the $O_2$ flow as indicated by the trend in the extent of expiratory recoil of the ventilator bellows. The exact flow of oxygen is almost impossible to ascertain and, as a result, there is constant oscillation in the oxygen flow. The required flows of such other gases as $N_2O$ and anesthetic vapor are impossible to set without knowing the total body absorption of the gas. Attempting to set the anesthetic flow rates by trial and error results in oscillation of anesthetic depth due to the long delays between changes in source gas concentrations and the development of a steady state gas concentration.

Knowing gas flux would allow for more accurate setting of source gas flows, a shorter feed-back loop, and thus more stable alveolar gas concentrations during anesthesia as well as less frequent adjustments of source gas concentration and flow. Patients would benefit by receiving the intended and appropriate doses of anesthesia.

With our method, the $O_2$ flow is readily determined as the $O_2$ flow=$O_2$ flux=$O_2$ consumption (in steady state)
$= SGF \times (F_S O_2 - F_E O_2)$ where $F_S O_2$ is the concentration of $O_2$ in the source gas and $F_E O_2$ is the concentration of $O_2$ in expired gas.

Calculating flux of any gas x when breathing via a circle circuit with low SGF and with $CO_2$ absorber in place i) When x is $CO_2$, and rebreathing of $CO_2$ is prevented by means of a $CO_2$ absorber in the circuit, equation (1) cannot be used and one needs to know the $\dot{V}_{Dan}$ to calculate $\dot{V}_A$ (as $\dot{V}_A = \dot{V}_E - \dot{V}_{Dan}$). Then, $CO_2$ flux=$\dot{V}_A \times (F_E CO_2 - F_I CO_2)$, but since $F_I CO_2 = 0$, $CO_2$ flux=$\dot{V}_A \times F_E CO_2$. Our method does not confer any benefits to the calculation of the flux of $CO_2$ when a rebreathing circuit includes a $CO_2$ absorber.

ii) For a rebreathing circuit that includes a $CO_2$ absorber, or for any CBC, and when x is any other gas:

$$\text{flux\_of\_gas\_x} = SGF(F_{EX} - F_{SX}) + (\dot{V}_E - \dot{V}_{Dan} - SGF)(F_{EX} - F_{RBX}) \quad (2)$$

where $F_{SX}$ is the concentration of x in the SGF entering the circuit and $F_{RBX}$ is the concentration of x in the expired limb of the circuit before the gas passes through the $CO_2$ absorber and mixes with gas coming out of the flowmeter.

Since $F_{EX} = F_{RBX}$, $$\text{Flux of } x = SGF(F_{EX} - F_{RBX}) \quad (3)$$

Note that the actual inhaled concentration of x is the flow-weighted average concentration of x in the mixed SGF and rebreathed gas. However, with our method, the complex measurement and calculation of the inhaled volume of x are unnecessary. To measure the flux of an anesthetic, the SGF is multiplied by the difference between the end tidal and SGF concentrations of x. The continuous measure of flux of any gas by this method allows one to easily calculate the changes in anesthetic gas absorption, and hence vaporizer setting required to maintain the same end tidal concentrations of anesthetic for any SGF, including that equal to $O_2$ consumption, which is defined as "dosed circuit" anesthesia.

Examples of Benefits of Applying These Methods:

$N_2O$ is an anesthetic gas used in over 95% of anesthetic procedures. It is used in ratios of 1:1 to 2:1 with $O_2$. It is relatively insoluble in blood and body tissues so that when used as an anesthetic, the tissues saturate quickly with small volumes of the gas and the tissue uptake of $N_2O$ approaches 0. Nevertheless, it is impossible with present art to know when tissues become saturated.

Therefore, $N_2O$ flow settings are not commonly changed throughout the operation. $N_2O$ is an environmental pollutant breaking down the ozone layer and costs 10 times as much as $O_2$. The continued flow of $N_2O$ at levels greater than the rate of absorption is not only a waste of $N_2O$, but also wastes the anesthetic vapor that is washed out of the circuit with the excess $N_2O$.

Knowing the exact flux of $N_2O$ as with our method would allow the anesthesiologist to turn down, or off, the $N_2O$ when the tissues become saturated with it (i.e., when the flux=0). One would expect that the tissues will become saturated in about 5 minutes. For a 2 hour anesthetic, this would represent a 95% saving; the longer the operation, the greater the saving.

Halothane, isoflurane, sevoflurane, and desflurane are inhalation anesthetic vapors. They have various costs ranging from a few cents per milliliter for halothane and isoflurane to about one dollar per meter for sevoflurane and desflurane. They are also environmental pollutants breaking down the ozone layer. These vapors enter the anesthetic circuits as part of SGF at various concentrations set by the anesthesiologist. Knowing the rate of absorption of these anesthetic vapors would allow the most efficient use of the anesthetics and the most precise control of the depth of anesthetic.

b) Outside the Operating Room:

With our method, a subject breathes spontaneously or is ventilated, via a CBC as described above, oxygen consumption is calculated as $$SGF \times (F_SO_2 - F_EO_2)$$

where SGF and $F_SO_2$ are deliberately set and therefore known, and $F_EO_2$ is measured from a rapid $O_2$ analyzer.

Oxygen consumption in response to exercise is an important measure of physical fitness. This is a standard test performed routinely around the world by cardio-respiratory assessment laboratories to test exercise capacity, cardiopulmonary fitness and nutritional status in patients as well as in athletes.

Oxygen consumption is one of the measures required to measure cardiac output by the Fick method.

FIGS. 9A, 9B, 10, and 11 illustrate flow and concentration curves for comparison to the "gold standard' of measuring flux (timed collection) to our method.

Figure 9B:
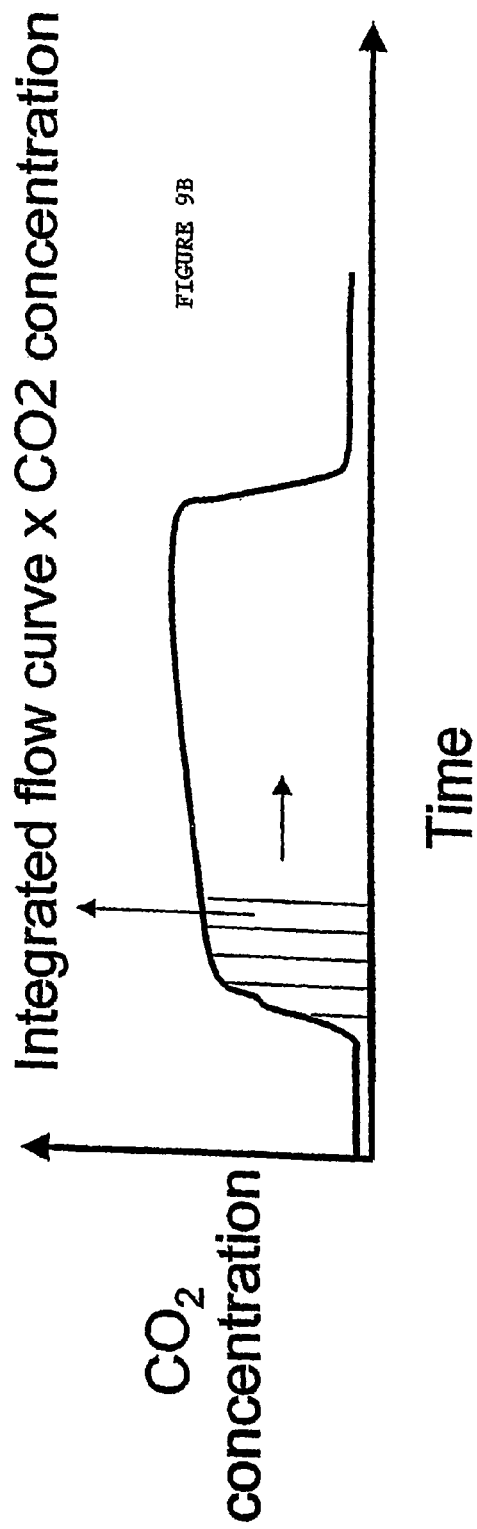

Particularly FIGS. 9A and 9B illustrate diagrams of flow and integrated concentration curves for carbon dioxide.

Figure 10:
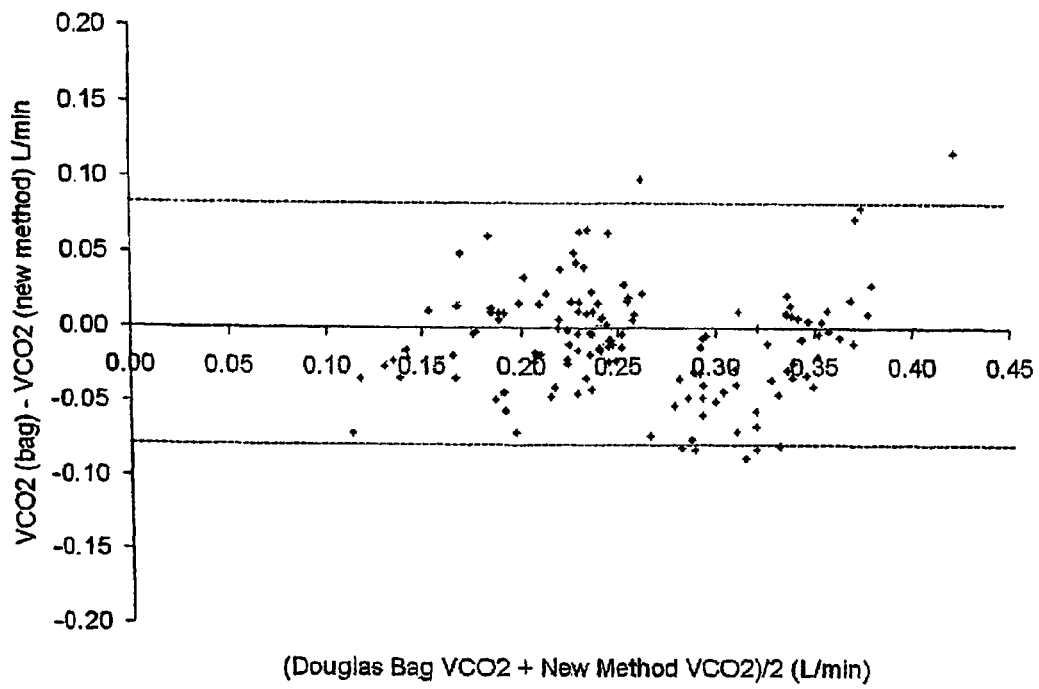
FIG. 10 illustrates with 95% confidence intervals the comparison of measurements of $\dot{V}_{CO_2}$ for the method of the present invention and the Douglas Bag collection method and differences between those measurements.

FIG. 10 illustrates with 95% confidence intervals the comparison of measurements of $\dot{V}_{CO_2}$ for the method of the present invention and the Douglas Bag collection method and differences between those measurements.

Figure 11:
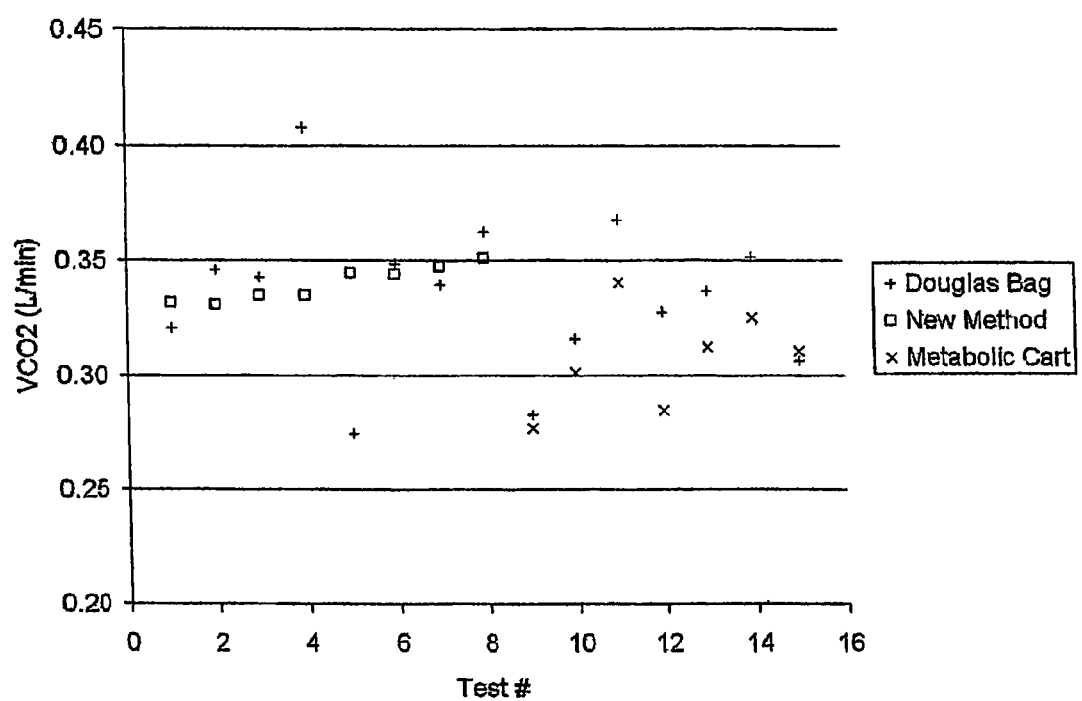
FIG. 11 illustrates a comparison of $\dot{V}_{CO_2}$ for the standard bag collection method, a metabolic cart and the method of the present invention.

FIG. 11 illustrates a comparison of $\dot{V}_{CO_2}$ for the standard bag collection method, a metabolic cart and the method of the present invention.

As many changes can be made to the various embodiments of the invention without departing from the scope thereof; it is intended that all matter contained herein be interpreted as illustrative of the invention but not in a limiting sense.

The embodiments of the invention in which an exclusive property or privilege is claimed are as follows:

1. A method of determining the flux of a gas "X" in a subject that is ventilated or breathing spontaneously, comprising the steps of:
  a. providing to the subject, via a Conditional Breathing Circuit (CBC), a source gas and a second gas that has substantially the same concentration of gas "X" as in the alveoli of the lung, wherein the source gas for a given breath is provided at a flow rate (SGF) that results in the source gas entering the CBC being equal to or less than the subject's alveolar ventilation, any balance of the gas provided for the same breath being the second gas;
  b. determining the flux of gas "X" by:
    (i) determining the source gas flow (SGF) into the CBC;
    (ii) determining the concentration, $F_{SX}$, of gas "X" in the source gas flow;
    (iii) determining the concentration, $F_{EX}$, of gas "X" in the end expired gas; and
    (iv) processing data utilizing the relationship:

Flux of gas "$X$" = $SGF(F_{SX} - F_{EX})$; or

Flux of gas "$X$" = $SGF(F_{EX} - F_{SX})$;

wherein:
    SGF=the rate of source gas flow into the CBC in liters/minute;
    $F_{SX}$=Fractional concentration of gas "X" in the source gas;
    $F_{EX}$=Fractional concentration of gas "X" in the end expired gas.

2. The method of claim 1, wherein the second gas is gas expired by the subject in the preceding breath.

3. The method of claim 2, wherein values for SGF, $F_{SX}$ and $F_{EX}$ are determined by a device comprising a gas flow meter and a tidal gas analyzer and wherein the data is processed by a processor operatively associated with the device.

4. The method of claim 1, wherein the Conditional Breathing Circuit is Magill circuit.

5. The method of claim 1, wherein the Conditional Breathing Circuit is a-rebreathing circuit.

6. The method of claim 1, wherein the CBC circuit is a non-rebreathing circuit.

7. The method of claim 2 used to determine oxygen consumption.

8. The method of claim 2 used to determine oxygen consumption in an operating room setting.

9. The method of claim 2 or 8 used to optimize oxygen consumption.

10. The method of claim 2 or 8 utilized as an early indication of malignant hyperthermia.

11. A method according to claim 1, wherein gas "X" is any gas other than carbon dioxide and wherein the Conditional Breathing Circuit (CBC) comprises a carbon dioxide absorber
and wherein the term $F_{EX}$ in the equation Flux of gas "X"=SGF ($F_{SX}-F_{EX}$) is replace by the term $F_{RBX}$
where $F_{RBX}$ =Concentration of gas X in the expired limb of circuit before the gas passes through the carbon dioxide absorber and mixes with gas coming from the flow meter.

12. The method of claim 11 used to determine how much anesthetic is being absorbed by the patient.

13. The method of claim 12 wherein said anesthetic is $N_2O$.

14. The method of claim 1, 2, or 11, wherein said method is incorporated in an algorithm spreadsheet, formula or the like contained within software which is capable of running on a computing device, or is installed therein.

15. The method of claim 1, wherein the gas "X" is carbon dioxide and the CBC is a re-breathing circuit.

16. The method of claim 11, wherein the gas "X" is an anesthetic and the CBC is a re-breathing circuit.

17. The method of claim 16, wherein the anesthetic is:
  i) $N_2O$;
  ii) sevoflurane;
  iii) isoflurane;
  iv) halothane;
  v) desflurane.

18. An apparatus configured for use with a Conditional Breathing Circuit (CBC) for determining the flux of a gas "X" in a subject that is ventilated or breathing spontaneously, comprising:
   c. at least one gas analyzer;
   d. a gas flow meter for determining the rate of flow of a source gas;
   e. a processor programmed for:
      (i) determining the source gas flow (SGF) into the CBC;
      (ii) determining the concentration, $F_{SX}$, of gas "X" in the source gas flow;
      (iii) determining the concentration, $F_{EX}$, of gas "X" in the expired gas; and
      (iv) processing data utilizing the relationship:

$$\text{Flux of gas ``}X\text{''}=SGF(F_{SX}-F_{EX}); \text{ or}$$

$$\text{Flux of gas ``}X\text{''}=SGF(F_{EX}-F_{SX});$$

wherein:
      SGF=the rate of source gas flow into the CBC in liters/minute;
      $F_{SX}$=Fractional concentration of gas "X" in the source gas;
      $F_{EX}$=Fractional concentration of gas "X" in the end expired gas.

19. An apparatus according to claim 18 in the form of an anesthetic machine wherein gas "X" is an anesthetic gas and wherein the CBC includes a carbon dioxide absorber and wherein the processor is configured to determine consumption of the anesthetic gas using the relationship Flux of gas "X"=SGF($F_{SX}$–$F_{EX}$) by determining $F_{RBX}$ and by replacing the term $F_{EX}$ in the equation Flux of gas "X"=SGF ($F_{SX}$–$F_{EX}$) by the term $F_{RBX}$;
   where $F_{RBX}$=Concentration of gas X in the expired limb of circuit before the gas passes through the carbon dioxide absorber and mixes with gas coming from the flow meter.

20. An apparatus according to claim 18 further comprising a CBC.

21. The use of a conditional breathing circuit (CBC) for determining the flux of a gas "X" in a subject that is ventilated or breathing spontaneously, comprising the steps of:
   a. analyzing the concentration of gas "X" in the end tidal gas;
   b. controlling the rate of flow of a source gas;
   c. determining the concentration, $F_{SX}$, of gas "X" in the source gas flow;
   d. processing data utilizing the relationship:

$$\text{Flux of gas ``}X\text{''}=SGF(F_{SX}-F_{EX}); \text{ or}$$

$$\text{Flux of gas ``}X\text{''}=SGF(F_{EX}-F_{SX});$$

wherein:
      SGF=the rate of source gas flow into the CBC in liters/minute;
      $F_{SX}$=Fractional concentration of gas "X" in the source gas;
      $F_{EX}$=Fractional concentration of gas "X" in the end expired gas.

22. A processor programmed for receiving source gas flow rate data and gas concentration data generated by a gas analyzer, and programmed for:
   (v) determining the source gas flow (SGF) into a CBC;
   (vi) determining the concentration, $F_{SX}$, of gas "X" in the source gas flow;
   (vii) determining the concentration, $F_{EX}$, of gas "X" in the expired gas; and
   (viii) processing data utilizing the relationship:

$$\text{Flux of gas ``}X\text{''}=SGF(F_{SX}-F_{EX}); \text{ or}$$

$$\text{Flux of gas ``}X\text{''}=SGF(F_{EX}-F_{SX});$$

wherein:
      SGF=the rate of source gas flow into the CBC in liters/minute;
      $F_{SX}$=Fractional concentration of gas "X" in the source gas;
      $F_{EX}$=Fractional concentration of gas "X" in the end expired gas.

23. The use according to claim 21, wherein gas "X" is an anesthetic gas and wherein the CBC includes a carbon dioxide absorber and wherein the data is processed to determine consumption of the anesthetic gas using the relationship: Flux of gas "X"=SGF ($F_{SX}$–$F_{EX}$) by determining $F_{RBX}$ and by replacing the term $F_{EX}$ in the equation Flux of gas "X"=SGF ($F_{SX}$–$F_{EX}$) by the term $F_{RBX}$;
   where $F_{RBX}$=Concentration of gas X in the expired limb of circuit before the gas passes through the carbon dioxide absorber and mixes with gas coming from the flow meter.

24. A processor according to claim 22, wherein gas "X" is an anesthetic gas and wherein the CBC includes a carbon dioxide absorber and wherein the data is processed to determine consumption of the anesthetic gas using the relationship: Flux of gas "X"=SGF ($F_{SX}$–$F_{EX}$) by determining $F_{RBX}$ and by replacing the term $F_{EX}$ in the equation Flux of gas "X"=SGF ($F_{SX}$–$F_{EX}$) by the term $F_{RBX}$;
   where $F_{RBX}$=Concentration of gas X in the expired limb of circuit before the gas passes through the carbon dioxide absorber and mixes with gas coming from the flow meter.

* * * * *